(12) United States Patent
Wu et al.

(10) Patent No.: US 12,097,280 B2
(45) Date of Patent: Sep. 24, 2024

(54) PERSONAL CARE COMPOSITIONS AND METHODS FOR THE SAME

(71) Applicant: Colgate-Palmolive Company, New York, NY (US)

(72) Inventors: Qiang Wu, Hillsborough, NJ (US); Laurence Du-Thumm, Princeton, NJ (US); Shujiang Cheng, Warren, NJ (US); Adriana Armas, Mexico City (MX); Luis Miguel Lopez, Mexico City (MX); Alejandro Meneses, Del.Miguel Hidalgo (MX)

(73) Assignee: Colgate-Palmolive Company, New York, NY (US)

( * ) Notice: Subject to any disclaimer, the term of this patent is extended or adjusted under 35 U.S.C. 154(b) by 825 days.

(21) Appl. No.: 17/250,385

(22) PCT Filed: Dec. 2, 2020

(86) PCT No.: PCT/US2020/070837
§ 371 (c)(1),
(2) Date: Jan. 14, 2021

(87) PCT Pub. No.: WO2021/127675
PCT Pub. Date: Jun. 24, 2021

(65) Prior Publication Data
US 2022/0401353 A1    Dec. 22, 2022

Related U.S. Application Data

(60) Provisional application No. 62/948,522, filed on Dec. 16, 2019.

(51) Int. Cl.
| | | |
|---|---|---|
| *A61K 36/00* | (2006.01) | |
| *A61K 8/92* | (2006.01) | |
| *A61K 8/9794* | (2017.01) | |
| *A61Q 19/10* | (2006.01) | |

(52) U.S. Cl.
CPC ............ *A61K 8/9794* (2017.08); *A61K 8/922* (2013.01); *A61Q 19/10* (2013.01)

(58) Field of Classification Search
CPC .................................................. A61Q 19/10
See application file for complete search history.

(56) References Cited

U.S. PATENT DOCUMENTS

| | | |
|---|---|---|
| 5,916,573 A | 6/1999 | Cleaves |
| 6,503,492 B2 | 1/2003 | McGlone et al. |
| 6,673,756 B2 | 1/2004 | Sonnenberg et al. |
| 8,147,883 B1 | 4/2012 | Msika et al. |
| 8,623,335 B2 | 1/2014 | Waddington |
| 8,920,853 B2 | 12/2014 | Darsale |
| 9,629,856 B2 | 4/2017 | Dreher |
| 9,867,774 B1* | 1/2018 | Hakim ..................... A61K 8/19 |
| 10,172,786 B2 | 1/2019 | Anastassov et al. |
| 10,456,345 B2 | 10/2019 | Ross |
| 10,806,692 B2 | 10/2020 | Guskey et al. |
| 10,806,769 B2 | 10/2020 | Tian et al. |
| 2003/0235550 A1 | 12/2003 | Pan et al. |
| 2005/0100524 A1 | 5/2005 | Springstead |
| 2005/0266103 A1* | 12/2005 | Yoder ..................... A61K 36/15 424/770 |
| 2006/0029657 A1 | 2/2006 | Popp et al. |
| 2007/0224154 A1 | 9/2007 | Brumbaugh et al. |
| 2008/0286390 A1 | 11/2008 | Tanyi |
| 2011/0264059 A1 | 10/2011 | Klofta et al. |
| 2012/0095087 A1 | 4/2012 | Hyatt |
| 2013/0230609 A1 | 9/2013 | Modak et al. |
| 2015/0182428 A1 | 7/2015 | Schmit |
| 2016/0235661 A1 | 8/2016 | Changoer et al. |
| 2016/0287658 A1 | 10/2016 | Son et al. |
| 2016/0317419 A1 | 11/2016 | Hakazaki et al. |
| 2016/0331675 A1* | 11/2016 | Jamerson ............. A61K 8/9789 |
| 2017/0000717 A1 | 1/2017 | Reynoso |
| 2017/0281718 A1 | 10/2017 | Tian et al. |
| 2018/0049971 A1 | 2/2018 | Druilhet |
| 2018/0263952 A1 | 9/2018 | Bíróet al. |
| 2018/0284402 A1 | 10/2018 | Hoag |
| 2019/0374552 A1 | 12/2019 | Hoag |

FOREIGN PATENT DOCUMENTS

| | | |
|---|---|---|
| CN | 1679505 | 10/2005 |
| CN | 1883449 | 12/2006 |
| CN | 101422200 | 5/2009 |

(Continued)

OTHER PUBLICATIONS

Tallaride, Quantitative methods for assessing drug synergism, Genes & Cancer 2(11) 1003-1008, 2011 (Year: 2011).*
Raskin et al., Can an apple a day keep the doctor away, Current Pharmaceutical Designs, 2004, 10: 3419-3429 (Year: 2004).*
Scalp-Wikipedia, accessed on Mar. 20, 2024, pp. 1-5 (Year: 2024).*
Aloe vera-Wikipedia, accessed on Mar. 20, 2024, pp. 1-11 (Year: 2024).*
Nindo et al, Thermal Properties of Aloe Vera Powder and Rheology of Reconstituted Gels. Transactions of the ASABE (2010), vol. 53, No. 4, pp. 1193-1200 (Year: 2010).*

(Continued)

*Primary Examiner* — Qiuwen Mi

(57) ABSTRACT

Personal care compositions and methods for treating one or more dry skin conditions are disclosed. The composition may include a carrier, one or more plant oils, and a source of *Aloe vera*. The one or more plant oils and the source of *Aloe vera* may each be present in an effective amount to increase natural moisturizing factors in skin when applied thereto. The method for treating the one or more dry skin conditions may include contacting the personal care composition with skin. Contacting the personal care composition with the skin may increase an amount of natural moisturizing factors in the skin and/or increase an amount of Caspase-14 in the skin.

18 Claims, No Drawings

(56) References Cited

FOREIGN PATENT DOCUMENTS

| | | | | |
|---|---|---|---|---|
| CN | 101843336 | | 9/2010 | |
| CN | 104371866 | A * | 2/2015 | |
| CN | 106074280 | | 11/2016 | |
| CN | 106420538 | A * | 2/2017 | |
| CN | 106620079 | | 5/2017 | |
| CN | 108541775 | | 9/2018 | |
| CN | 108619048 | A * | 10/2018 | |
| CN | 108635267 | | 10/2018 | |
| CN | 108703930 | A * | 10/2018 | ........... A61K 8/4946 |
| CN | 108785192 | | 11/2018 | |
| CN | 108977290 | | 12/2018 | |
| CN | 110115706 | | 8/2019 | |
| EP | 0514576 | | 11/1992 | |
| EP | 1561457 | | 8/2005 | |
| EP | 2444081 | | 4/2012 | |
| EP | 2404502 | | 9/2013 | |
| EP | 3159012 | | 4/2017 | |
| FR | 2956580 | | 8/2011 | |
| FR | 2965477 | | 4/2012 | |
| KR | 2003074510 | A * | 9/2003 | |
| RO | 126918 | | 12/2011 | |
| RU | 2459614 | | 8/2012 | |
| RU | 2664694 | | 8/2018 | |
| WO | 1999/027904 | | 6/1999 | |
| WO | 2010/067206 | | 6/2010 | |
| WO | 2013/149323 | | 10/2013 | |
| WO | 2016/176485 | | 11/2016 | |
| WO | 2016/197015 | | 12/2016 | |
| WO | 2017/011785 | | 1/2017 | |
| WO | 2017/173240 | | 10/2017 | |
| WO | 2017/175126 | | 10/2017 | |
| WO | 2017/178937 | | 10/2017 | |
| WO | 2018/183151 | | 10/2018 | |
| WO | 2019/136351 | | 7/2019 | |
| WO | 2019/186544 | | 10/2019 | |
| WO | 2019/234743 | | 12/2019 | |
| WO | 2020/028991 | | 2/2020 | |

OTHER PUBLICATIONS

International Search Report and the Written Opinion of the International Searching Authority issued in International Application PCT/US2018/062411 mailed Jun. 13, 2019.
Reinholtz et al., 2012, "Cathelicidin LL-37: An Antimicrobial Peptide with a Role in Inflammatory Skin Disease," Ann Dermatology 24(2):126-135.
Oroian et al., "Antioxidants Characterization, Natural Sources, Extraction and Analysis", Food Research International, 74 (2015) 10-36.
Yang et al., "Synthesis of pyrrolidone carboxylic acid", Applied Chemical Industry, vol. 45, No. 4, Apr. 2016.
International Search Report and the Written Opinion of the International Searching Authority issued in International Application PCT/US2020/070614 mailed Jan. 25, 2021.
Qiu, Bingyi, Modern Cosmetic Science and Technology, vol. III, China Light Industry Press, Mar. 31, 2016, p. 727.
Babaria, 2019, "48H Antiperspirant Deo", Mintel Database GNPD AN:6734525.
Cozietic, 2018, "Deodorant Spray", Mintel Database GNPD AN: 6211729.
Dr. Organic, 2015, "Deodorant Roll-On", Mintel Database GNPD AN:3560879.
National Medical Products Administration, 2021, "Technical Specification for Cosmetic Safety (Revised 2021 Edition)", pp. 1-8.
Esika, 2016, "Youth Activating Concentrated Facial Serum", Mintel Database GNPD AN: 4394087.
Esika, 2017, "Day Anti-Ageing Facial Global Treatment SPF 25", Mintel Database GNPD AN: 4778185.
High Beauty, 2019, "High Five Cannabis Facial Moisturizer", Mintel Database GNPD AN: 7038029.
International Search Report and the Written Opinion of the International Searching Authority issued in International Application PCT/US2020/070771 mailed Feb. 24, 2021.
International Search Report and the Written Opinion of the International Searching Authority issued in International Application PCT/US2020/070837 mailed Mar. 29, 2021.
International Search Report and the Written Opinion of the International Searching Authority issued in International Application PCT/US2020/070849 mailed Mar. 11, 2021.
International Search Report and the Written Opinion of the International Searching Authority issued in International Application PCT/US2020/070851 mailed Mar. 4, 2021.
Purity Cosmetics, 2016, "Repair Eye Cream", Mintel Database GNPD AN: 4274053
Votary, 2019, "Super Boost Night Drops" Mintel Database GNPD AN: 6841777.
Shigabieva, 2014, "Colloidal-chemical properties of foaming and gel compositions with biologically active components: dissertation," Candidate of Chemical Sciences: 02.00.11.—Kazan, 2014.—158 p., pp. 8, 10, 113, chapter 1.3.
Shay & Company, 2023, https://shayandcompany.com/product/hemp-seed-butter-refined-non-gmo-halal/.
Singh et al. 2008, "Evaluation of anti-inflammatory activity of plant lipids containing a-linolenic acid," Indian Journal of Experimental Biology, 46:453-456.
Watzl et al. 1991, "Marijuana components stimulate human peripheral blood mononuclear cell secretion of interferon-gamma and suppress interleukin-1 alpha in vitro," International Journal of Immunopharmacology, 13(8):1091-1097.
Styrczewska et al., 2015, "Flax fiber hydrophobic extract inhibits human skin cells inflammation and causes remodeling of extracellular matrix and wound closure activation," BioMed Research International, 2015:1-15.
Anonymous, "Flax," last edited Jan. 3, 2024; Wikipedia, https://en.wikipedia.org/wiki/Flax.
Anonymous, "Hemp," last edited Mar. 3, 2024; Wikipedia, https://en.wikipedia.org/wiki/Hemp.
China National Institutes for Food and Drug Control, "The Announcement on Updating the Catalog of Raw Materials Banned for Cosmetics," National Medical Products Administration, (No. 74 of 2021), published May 28, 2021, pp. 1-6.

* cited by examiner

PERSONAL CARE COMPOSITIONS AND METHODS FOR THE SAME

BACKGROUND

Washing and cleaning skin with personal cleansing compositions (e.g., bar soaps, shower gels, body washes, cleansing lotions, liquid soaps, etc.) may often leave the skin feeling dry. For example, conventional cleansing compositions may often include one or more surfactants, perfumes, preservatives, antimicrobial agents, and the like, that may strip moisture from the skin, thereby leaving the skin feeling overly dry or chapped.

In view of the foregoing, moisturizers (e.g., emollients) may often be added to the cleansing compositions and/or lotions may be applied direct to the skin after washing to replenish, condition, and/or prevent excess dryness of the skin. While the moisturizers may attempt to restore or replenish some of the moisture stripped from the skin by conventional cleansing compositions, the moisturizers will not treat the skin by reversing the damage already caused by the components of the conventional cleansing compositions. For example, the moisturizers included in the cleansing compositions do not promote or enhance the production of natural moisturizing factors (NMFs) in the skin to thereby treat or allow the skin to regulate its hydration and repair any damage.

What is needed, then, are improved personal care compositions or personal cleansing compositions and methods for increasing the production of natural moisturizing factors in skin.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a personal care or personal cleansing composition including a carrier, one or more plant oils, and a source of *Aloe vera*.

In at least one example, the source of *Aloe vera* and the one or more plant oils may each be present in an effective amount to increase natural moisturizing factors in skin when applied to the skin.

In at least one example, the one or more plant oils may be present in an amount of from about 0.01 weight % to about 5 weight %, about 0.5 weight % to about 4.5 weight %, or about 2 weight % to about 3 weight %, based on a total weight of the personal care composition.

In at least one example, the source of *Aloe vera* may be present in an amount of from about 0.01 weight % to about 5 weight %, about 0.5 weight % to about 4.5 weight %, or about 2 weight % to about 3 weight %, based on a total weight of the personal care composition.

In at least one example, the one or more plant oils may include any one or more of palm kernel oil, coconut oil, avocado oil, canola oil, corn oil, cottonseed oil, olive oil, palm oil, high-oleic sunflower oil, mid-oleic sunflower oil, sunflower oil, palm stearin oil, palm kernel olein oil, safflower oil, babassu oil, sweet almond oil, castor oil, canola oil, soybean oil, olive oil, acai oil, andiroba oil, apricot kernel oil, argan oil, passion fruit oil, manila oil, mango oil, shea oil, macadamia nut oil, brazil nut oil, borage oil, copaiba oil, grape seed oil, buriti oil, sesame oil, flaxseed oil, blueberry oil, cranberry oil, blackberry oil, plum oil, raspberry oil, camelina oil, camellia oil, walnut oil, wheat germ oil, calendula oil, cherry kernel oil, cucumber seed oil, papaya oil, *Aloe vera* oil, hemp oil, or combinations thereof.

In at least one example, the one or more plant oils include flaxseed oil. In another example, the one or more plants consists essentially of flaxseed oil. In yet another example, the one or more plant oils consist of flaxseed oil.

In at least one example, the source of *Aloe vera* includes *Aloe vera*.

In at least one example, the source of *Aloe vera* includes an *Aloe vera* extract.

In at least one example, the source of *Aloe vera* includes a combination of *Aloe vera* and an *Aloe vera* extract.

In at least one example, the one or more plant oils and the source of *Aloe vera* are present in an effective ratio to increase natural moisturizing factors in the skin when applied to the skin, optionally, the one or more plant oils and the source of *Aloe vera* are present in a ratio of from about 0.1:1 to about 2:1, preferably from about 0.5:1 to about 1.5:1, more preferably about 1:1.

In at least one example, the personal care composition is a personal cleansing composition, optionally, the personal cleansing composition is a shower gel or a bar soap.

In at least one example, the carrier is a solid carrier. In another example, the carrier is a liquid carrier.

The foregoing and/or other aspects and utilities embodied in the present disclosure may be achieved by providing a method for preparing any one or more of the personal care compositions disclosed herein. The method may include contacting the one or more plant oils, the source of *Aloe vera*, and the carrier with one another.

The foregoing and/or other aspects and utilities embodied in the present disclosure may be achieved by providing a method for treating one or more dry skin conditions. The method may include contacting skin with any one or more of the personal care compositions disclosed herein.

In at least one example, contacting skin with any one or more of the personal care compositions disclosed herein increases an amount of natural moisturizing factors in or on the skin.

In at least one example, contacting the skin with any one or more of the personal care compositions disclosed herein increases an amount of Caspase-14 in or on the skin.

In at least one example, the method may include determining the presence of the one or more dry skin conditions, or diagnosing the one or more dry skin conditions. Determining the presence of the one or more dry skin conditions may include measuring a deficiency of filaggrin, natural moisturizing factors, and/or Caspase-14 levels in skin. In one example, the deficiency of filaggrin, natural moisturizing factors, and/or Caspase-14 levels in skin may be measured relative to a population baseline value. In another example, the deficiency of filaggrin, natural moisturizing factors, and/or Caspase-14 levels in skin may be measured relative to an individual baseline value.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any embodiments or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight %, based on a total weight of the composition, component, or phase.

All references cited herein are hereby incorporated by reference in their entireties. In the event of a conflict in a definition in the present disclosure and that of a cited reference, the present disclosure controls.

The present inventors have surprisingly and unexpectedly discovered that personal care products and personal care compositions thereof, including a carrier, one or more plant oils, and a source of *Aloe vera* significantly and unexpectedly increased the amount of Caspase-14; and thus, increased the production of natural moisturizing factors (NMFs) in the skin. As further demonstrated herein, the observed increase in Caspase-14 is especially surprising and unexpected as each of flaxseed oil and *Aloe vera*, when evaluated separately, resulted in a decrease in Caspase-14 in skin.

The present inventors have also surprisingly and unexpectedly discovered that personal care products and personal care compositions thereof, including a carrier, one or more plant oils, and a source of *Aloe vera* significantly and unexpectedly increased the amount of Caspase-14; and thus, increased the production of natural moisturizing factors (NMFs) in the skin when the plant oil (e.g., flaxseed oil) is present in an amount of about 0.5 wt % and the source of *Aloe vera* is present in an amount of from about 0.125 wt % or greater to about 1 wt % or less.

The present inventors have also surprisingly and unexpectedly discovered that personal care products and personal care compositions thereof, including a carrier, one or more plant oils, and a source of *Aloe vera* significantly and unexpectedly increased the amount of Caspase-14; and thus, increased the production of natural moisturizing factors (NMFs) in the skin when the plant oil (e.g., flaxseed oil) and the source of *Aloe vera* is present in a ratio of from about 1:0.25 or greater to about 1:2 or less.

COMPOSITIONS

Compositions disclosed herein may be or include a personal care product or a personal care composition thereof. For example, compositions disclosed herein may be a personal care composition, a personal care product, or form a portion of the personal care composition or the personal care product. As used herein, the term or expression "personal care composition" may refer to a composition for topical application to skin of mammals, especially humans. The personal care composition may generally be a leave-on personal care composition or rinse off personal care composition, and may include any product applied to a human body. The personal care composition is preferably a leave-on personal care composition. The personal care composition may be in any suitable form. Illustrative forms of the personal care composition may be or include, but is not limited to, a liquid, a lotion, a cream, a foam, a scrub, a gel, a soap bar, a toner, a substance or composition applied with an implement or via a face mask, or the like. Illustrative personal care compositions may be or include, but are not limited to, cleansers, leave-on skin lotions or creams, emulsion, shampoos, conditioners, shower gels, antiperspirants, deodorants, depilatories, lipsticks, foundations, mascara, sunless tanners, sunscreen lotions, body washes, soaps, including bar soaps and liquid soaps (e.g., liquid hand soaps), face washes, moisturizers, serums, spot treatments, cosmetics, or the like.

In an exemplary implementation, the compositions disclosed herein may be personal care compositions including a carrier, one or more plant oils, and a source of *Aloe vera*. In one example, the personal care composition may include a single plant oil. In another example, the personal care composition may include at least two plant oils. In a preferred implementation, the one or more plant oils includes at least flaxseed oil.

The personal care compositions disclosed herein may be capable of or configured to facilitate, promote, enhance, or otherwise increase the production or formation of natural moisturizing factors (NMFs) in skin, thereby increasing hydration and barrier functions of the skin. As such, the personal care compositions disclosed herein may be utilized in the treatment of any one or more dry skin conditions.

Illustrative dry skin conditions may be or include, but are not limited to, atoptic dermatitis, rosacea, psoriasis, or the like, or any combination thereof.

The personal care compositions disclosed herein may have a basic pH. For example, the personal care composition may have a pH of greater than 7 and less than or equal to about 11. In another example, the personal care composition may have a pH of from about 7.5, about 8, about 8.5, or about 9 to about 9.5, about 10, about 10.5, about 11, or about 11.5. In yet another example, the personal care composition may have a pH of from about 7.5 to about 11.5, about 8 to about 11, or about 9 to about 10. It should be appreciated that personal care compositions having a basic or relatively high pH (e.g., pH of about 9 to about 10) may generally deplete, strip, or otherwise reduce lipids in the skin and/or cause irritation of the skin. A such, providing a moisturizing benefit to personal care compositions, such as bar soaps, having a basic or relatively high pH (e.g., pH of about 9 to about 10) is not only beneficial, but challenging.

The personal care composition may include a source of *Aloe vera*. The source of *Aloe vera* may be or include *Aloe vera*, an *Aloe vera* extract, or combinations thereof. The *Aloe vera* extract may be a leaf extract of the *Aloe vera* plant, which is a cactus plant that belongs to the Liliaceae family. As used herein, "*Aloe vera*" may refer to the plant *Aloe vera* Linne, sometimes referred to as *Aloe barbadensis* Miller, which is known to those skilled in the art to be the variety of the *Aloe vera* plant used in the cosmetic industry. As used herein, "*Aloe vera* extract" may refer to a liquid extract, a gel obtained directly from the leaves of the *Aloe vera* plant, and/or a gel reconstituted from powdered *Aloe vera* extract. *Aloe vera* extract in the form of a gel may be obtained directly from the thin-walled tubular cells from the inner central zone of the leaf (mucilaginous parenchyma) of the *Aloe vera* Linne plant. The *Aloe vera* gel may be dried and/or powdered. For example, the *Aloe vera* gel may be lyophilized.

The *Aloe vera* and/or an extract thereof may be present in the personal care composition in an effective amount or a therapeutically effective amount. As used herein, the expression or term "effective amount of a source of *Aloe vera*," "effective amount of *Aloe vera* and/or an extract thereof," or the like may refer to an amount of *Aloe vera* and/or an extract thereof sufficient to interact or work synergistically with the one or more plant oils to elicit a response (e.g., biological, medical, etc.) of a tissue, system, animal, or human that is being sought. For example, the *Aloe vera* and/or an extract thereof may be present in the personal care composition in an effective amount to interact or work synergistically with the one or more plant oils to increase the production of NMFs and/or Caspase-14 in skin.

The amount or concentration of the *Aloe vera* and/or an extract thereof present in the personal care composition may vary widely. In at least one implementation, the *Aloe vera* and/or an extract thereof may be present in the personal care composition in an amount sufficient to deliver an effective amount and/or ratio, as disclosed herein, of the *Aloe vera* and/or an extract thereof to skin cells when applied to an outer surface of the skin or outer dermis. It should be appreciated that the amount of the *Aloe vera* and/or an extract thereof present in the personal care composition may be relatively greater than the effective amount, as penetration of the *Aloe vera* and/or an extract thereof from the outer dermis to the skin cells may be at least partially determined by varying factors, as is known by those having ordinary skill in the art.

In at least one implementation, the amount of the source of *Aloe vera* present in the personal care composition may be from greater than 0 weight % to less than or equal to 40 weight %, based on a total weight of the personal care composition. For example, the *Aloe vera* and/or an extract thereof may be present in the personal care composition in an amount of from greater than 0 weight %, about 0.01 weight %, about 0.1 weight %, about 0.125 wt %, about 0.2 weight %, about 0.3 weight %, about 0.4 weight %, about 0.5 weight %, about 0.6 weight %, about 0.7 weight %, about 0.8 weight %, about 0.9 weight %, about 1 weight %, about 1.2 weight %, about 1.4 weight %, about 1.6 weight %, about 1.8 weight %, about 2 weight %, about 3 weight %, about 4 weight %, about 5 weight %, about 6 weight %, about 7 weight %, about 8 weight %, about 9 weight %, about 10 weight %, about 15 weight %, or about 20 weight % to about 25 weight %, about 30 weight %, about 35 weight %, about 40 weight %, based on a total weight of the personal care composition. In another example, the *Aloe vera* and/or an extract thereof may be present in the personal care composition in an amount of at least 0.00001 wt %, at least 0.0001 weight %, at least 0.001 weight %, at least 0.01 weight %, at least 0.1 weight %, at least 1.0 weight %, at least 1.5 weight %, at least 2.0 weight %, at least 2.5 weight %, at least 3.0 weight %, at least 3.5 weight %, at least 4.0 weight %, at least 5 weight %, at least 10 weight %, at least 20 at least %, at least 30 weight %, or more, based on a total weight of the personal care composition. In yet another example, the *Aloe vera* and/or an extract thereof may be present in the personal care composition in an amount of from greater than 0 weight % to less than 40 weight %, less than 35 weight %, less than 30 weight %, less than 25 weight %, less than 20 weight %, less than 15 weight %, less than 10 weight %, less than 9 weight %, less than 8 weight %, less than 7 weight %, less than 6 weight %, less than 5 weight %, less than 4 weight %, less than 3 weight %, less than 2 weight %, less than 1 weight %, less than 0.1 weight %, or less than 0.01 weight %, based on a total weight of the personal care composition. In yet another example, the *Aloe vera* and/or an extract thereof may be present in the personal care composition in an amount of from greater than 0 weight % to about 5 weight %, about 0.01 weight % to about 5 weight %, about 0.1 weight % to about 4.9 weight %, about 0.2 weight % to about 4.8 weight %, about 0.3 weight % to about 4.7 weight %, about 0.4 weight % to about 4.6 weight %, about 0.5 weight % to about 4.5 weight %, about 0.6 weight % to about 4.4 weight %, about 0.7 weight % to about 4.3 weight %, about 0.8 weight % to about 4.2 weight %, about 0.9 weight % to about 4.1 weight %, about 1 weight % to about 4 weight %, about 1.2 weight % to about 3.8 weight %, about 1.4 weight % to about 3.6 weight %, about 1.6 weight % to about 3.4 weight %, about 1.8 weight % to about 3.2 weight %, about 2 weight % to about 3 weight %, about 2.2 weight % to about 2.8 weight %, or about 2.4 weight % to about 2.6 weight %, based on a total weight of the personal care composition. In a preferred implementation, the *Aloe vera* and/or an extract thereof may be present in an amount of from about 0.125 wt % or greater to about 1 wt % or less, preferably about 0.150 wt % to about 0.80 wt %, or more preferably about 0.2 wt % to about 0.7 wt %, based on a total weight of the personal care composition.

The personal care composition may include one or more plant oils. For example, the personal care composition may include a single plant oil or a combination of two or more plant oils. As used herein, "plant oil" may refer to a natural oil that is completely obtained from a plant, or a manufactured oil made by blending at least two components of oil (e.g., triglycerides, saturated and/or unsaturated fatty acids, etc.) to substantially mimic the composition of a natural plant oil or provide an oil substantially similar in composition to a plant oil. For example, a manufactured oil substantially similar in composition to a plant oil may include at least 50 weight %, at least 60 weight %, at least 70 weight %, at least 80 weight %, at least 90 weight %, at least 95 weight %, at least 98 weight %, at least 99 weight %, at least 99.5 weight %, at least 99.9 weight %, or 100 weight % of the components that are naturally found in the plant oil that the manufactured oil is designed to substantially mimic.

Illustrative plant oils may be or include, but are not limited to, palm kernel oil, coconut oil, avocado oil, canola oil, corn oil, cottonseed oil, olive oil, palm oil, high-oleic sunflower oil, mid-oleic sunflower oil, sunflower oil, palm stearin oil, palm kernel olein oil, safflower oil, babassu oil, sweet almond oil, castor oil, canola oil, soybean oil, olive oil, acai oil, andiroba oil, apricot kernel oil, argan oil, passion fruit oil, manila oil, mango oil, shea oil, macadamia nut oil, brazil nut oil, borage oil, copaiba oil, grape seed oil, buriti oil, sesame oil, flaxseed oil or linseed oil, blueberry oil, cranberry oil, blackberry oil, plum oil, raspberry oil, camelina oil, camellia oil, walnut oil, wheat germ oil, calendula oil, cherry kernel oil, cucumber seed oil, papaya oil, *Aloe vera* oil, hemp oil, hemp seed oil, or the like, or mixtures or combinations thereof. In a preferred implementation, the plant oil includes flaxseed or linseed oil.

The one or more plant oils may be present in the personal care composition in an effective amount or a therapeutically effective amount. As used herein, the expression or term "effective amount of one or more plant oils" or the like may refer to an amount of the one or more plant oils sufficient to interact or work synergistically with the source of *Aloe vera* to elicit a response (e.g., biological, medical, etc.) of a tissue, system, animal, or human that is being sought. For example, the one or more plant oils may be present in the personal care composition in an effective amount to interact or work synergistically with the *Aloe vera* and/or an extract thereof to increase the production of NMFs and/or Caspase-14 in skin.

The amount or concentration of any one or more of the plant oils present in the personal care composition may vary widely. In at least one implementation, any one or more of the plant oils may be present in the personal care composition in an amount sufficient to deliver an effective amount and/or ratio, as disclosed herein, of the one or more plant oils to skin cells when applied to an outer surface of the skin or outer dermis. It should be appreciated that the amount and/or ratio of the one or more plant oils present in the in the personal care composition may be relatively greater than the effective amount, as penetration of the one or more plant oils from the outer dermis to the skin cells may be at least partially determined by varying factors, as is known by those having ordinary skill in the art.

In at least one implementation, the amount of any one or more of the plant oils (e.g., each or a combination) present in the personal care composition may be from greater than 0 weight % to less than or equal to 40 weight %, based on a total weight of the personal care composition. For example, any one or more of the plant oils may be present in the personal care composition in an amount of from greater than 0 weight %, about 0.01 weight %, about 0.1 weight %, about 0.2 weight %, about 0.3 weight %, about 0.4 weight %, about 0.5 weight %, about 0.6 weight %, about 0.7 weight %, about 0.8 weight %, about 0.9 weight %, about 1 weight %, about 1.2 weight %, about 1.4 weight %, about 1.6 weight %, about 1.8 weight %, about 2 weight %, about 3 weight %, about 4 weight %, about 5 weight %, about 6 weight %, about 7 weight %, about 8 weight %, about 9 weight %, about 10 weight %, about 15 weight %, or about 20 weight % to about 25 weight %, about 30 weight %, about 35 weight %, about 40 weight %, based on a total weight of the personal care composition. In another example, any one or more of the plant oils may be present in the personal care composition in an amount of at least 0.00001 wt %, at least 0.0001 weight %, at least 0.001 weight %, at least 0.01 weight %, at least 0.1 weight %, at least 1.0 weight %, at least 1.5 weight %, at least 2.0 weight %, at least 2.5 weight %, at least 3.0 weight %, at least 3.5 weight %, at least 4.0 weight %, at least 5 weight %, at least 10 weight %, at least 20 at least %, at least 30 weight %, or more, based on a total weight of the personal care composition. In yet another example, any one or more of the plant oils may be present in the personal care composition in an amount of from greater than 0 weight % to less than 40 weight %, less than 35 weight %, less than 30 weight %, less than 25 weight %, less than 20 weight %, less than 15 weight %, less than 10 weight %, less than 9 weight %, less than 8 weight %, less than 7 weight %, less than 6 weight %, less than 5 weight %, less than 4 weight %, less than 3 weight %, less than 2 weight %, less than 1 weight %, less than 0.1 weight %, or less than 0.01 weight %, based on a total weight of the personal care composition. In yet another example, any one or more of the plant oils may be present in the personal care composition in an amount of from greater than 0 weight % to about 5 weight %, about 0.01 weight % to about 5 weight %, about 0.1 weight % to about 4.9 weight %, about 0.2 weight % to about 4.8 weight %, about 0.3 weight % to about 4.7 weight %, about 0.4 weight % to about 4.6 weight %, about 0.5 weight % to about 4.5 weight %, about 0.6 weight % to about 4.4 weight %, about 0.7 weight % to about 4.3 weight %, about 0.8 weight % to about 4.2 weight %, about 0.9 weight % to about 4.1 weight %, about 1 weight % to about 4 weight %, about 1.2 weight % to about 3.8 weight %, about 1.4 weight % to about 3.6 weight %, about 1.6 weight % to about 3.4 weight %, about 1.8 weight % to about 3.2 weight %, about 2 weight % to about 3 weight %, about 2.2 weight % to about 2.8 weight %, or about 2.4 weight % to about 2.6 weight %, based on a total weight of the personal care composition. In a preferred implementation, any one or more of the plant oils (e.g., flaxseed oil) may be present in an amount of from greater than 0 wt % or 0.01 wt % to about 1 wt %, preferably about 0.25 wt % to about 0.75 wt %, or more preferably about 0.5 wt %, based on a total weight of the personal care composition.

The personal care composition may include a synergistic combination of the one or more plant oils and the source of *Aloe vera*. For example, the personal care composition may include a synergistic combination of flaxseed oil and *Aloe vera* and/or an extract thereof. In at least one implementation, the one or more plant oils and the source of *Aloe vera* (i.e., *Aloe vera* and/or an extract thereof) may be present in an effective ratio (i.e., concentration, weight, or volume ratio) or a therapeutically effective ratio (i.e., concentration, weight, or volume ratio) to elicit a response (e.g., biological medical, etc.) of a tissue, system, animal, or human that is being sought. For example, a plant oil, such as flaxseed oil, and the *Aloe vera* and/or an extract thereof may be present in an effective concentration, weight, or volume ratio or a therapeutically effective concentration, weight, or volume ratio to interact or work synergistically with one another to increase the production of NMFs and/or Caspase-14 in skin.

In at least one implementation, the concentration, weight, or volume ratio of the one or more plant oils to the source of *Aloe vera* (i.e., *Aloe vera* and/or an extract thereof) may be from about 0.1:1 to about 5:1. For example, the concentration, weight, or volume ratio of the one or more plant oils to the source of *Aloe vera* may be from about 0.1:1, about 0.2:1, about 0.3:1, about 0.4:1, about 0.5:1, about 0.6:1, about 0.7:1, about 0.8:1, about 0.9:1, or about 1.0:1 to about 1.1:1, about 1.2:1, about 1.3:1, about 1.4:1, about 1.5:1, about 1.6:1, about 1.7:1, about 1.8:1, about 1.9:1, about 2.0:1, about 2.1:1, about 2.2:1, about 2.3:1, about 2.4:1, about 2.5:1, about 2.6:1, about 2.7:1, about 2.8:1, about 2.9:1, about 3.0:1, about 3.1:1, about 3.2:1, about 3.3:1, about 3.4:1, about 3.5:1, about 3.6:1, about 3.7:1, about 3.8:1, about 3.9:1, about 4:1, about 4.1:1, about 4.2:1, about 4.3:1, about 4.4:1, about 4.5:1, about 4.6:1, about 4.7:1, about 4.8:1, about 4.9:1, or about 5:1. In another example, the concentration, weight, or volume ratio of the one or more plant oils to the source of *Aloe vera* may be from greater than or equal to about 0.1:1 to less than or equal to about 0.2:1, less than or equal to about 0.3:1, less than or equal to about 0.4:1, less than or equal to about 0.5:1, less than or equal to about 0.6:1, less than or equal to about 0.7:1, less than or equal to about 0.8:1, less than or equal to about 0.9:1, less than or equal to about 1.0:1, less than or equal to about 1.1:1, less than or equal to about 1.2:1, less than or equal to about 1.3:1, less than or equal to about 1.4:1, less than or equal to about 1.5:1, less than or equal to about 1.6:1, less than or equal to about 1.7:1, less than or equal to about 1.8:1, less than or equal to about 1.9:1, less than or equal to about 2.0:1, less than or equal to about 2.1:1, less than or equal to about 2.2:1 to less than or equal to about 2.3:1, less than or equal to about 2.4:1, less than or equal to about 2.5:1, less than or equal to about 2.6:1, less than or equal to about 2.7:1, less than or equal to about 2.8:1, less than or equal to about 2.9:1, less than or equal to about 3.0:1, less than or equal to about 3.1:1, less than or equal to about 3.2:1, less than or equal to about 3.3:1, less than or equal to about 3.4:1, less than or equal to about 3.5:1, less than or equal to about 3.6:1, less than or equal to about 3.7:1, less than or equal to about 3.8:1, less than or equal to about 3.9:1, less than or equal to about 4:1, less than or equal to about 4.1:1, less than or equal to about 4.2:1, less than or equal to about 4.3:1, less than or equal to about 4.4:1, less than or equal to about 4.5:1, less than or equal to about 4.6:1, less than or equal to about 4.7:1, less than or equal to about 4.8:1, less than or equal to about 4.9:1, or less than or equal to about 5:1. In yet another example, the concentration, weight, or volume ratio of the one or more plant oils to the source of *Aloe vera* may be from greater than or equal to about 0.1:1, greater than or equal to about 0.2:1, greater than or equal to about 0.3:1, greater than or equal to about 0.4:1, greater than or equal to about 0.5:1, greater than or equal to about 0.6:1, greater than or equal to about 0.7:1, greater than or equal to about 0.8:1, greater than or equal to about 0.9:1, greater than or equal to about 1.0:1, greater than or equal to about 1.1:1, greater than or equal to about 1.2:1, greater than or equal to about 1.3:1, greater than or equal to about 1.4:1, greater than or equal to about 1.5:1, greater than or equal to about 1.6:1, greater than or equal to about 1.7:1, greater than or equal to about 1.8:1, greater than or equal to about 1.9:1, greater than or equal to about 2.0:1, greater than or equal to about 2.1:1, greater than or equal to about 2.2:1 to greater than or equal to about 2.3:1, greater than or equal to about 2.4:1, greater than or equal to about 2.5:1, greater than or equal to about 2.6:1, greater than or equal to about 2.7:1, greater than or equal to about 2.8:1, greater than or equal to about 2.9:1, greater than or equal to about 3.0:1, greater than or equal to about 3.1:1, greater than or equal to about 3.2:1, greater than or equal to about 3.3:1, greater than or equal to about 3.4:1, greater than or equal to about 3.5:1, greater than or equal to about 3.6:1, greater than or equal to about 3.7:1, greater than or equal to about 3.8:1, greater than or equal to about 3.9:1, greater than or equal to about 4:1, greater than or equal to about 4.1:1, greater than or equal to about 4.2:1, greater than or equal to about 4.3:1, greater than or equal to about 4.4:1, greater than or equal to about 4.5:1, greater than or equal to about 4.6:1, greater than or equal to about 4.7:1, greater than or equal to about 4.8:1, or greater than or equal to about 4.9:1 to less than or equal to about 5:1. In a particular implementation, the concentration, weight, or volume ratio of the one or more plant oils to the source of *Aloe vera* may be from about or greater than 1:0.25 to about or less than 1:2, more preferably from about 1:0.35 to about 1:1.75, even more preferably about 1:0.5 to about 1:1.5. For example, the concentration, weight, or volume ratio of flaxseed oil to the source of *Aloe vera* may be from about or greater than 1:0.25 to about or less than 1:2, more preferably from about 1:0.35 to about 1:1.75, even more preferably about 1:0.5 to about 1:1.5.

The total amount of active ingredients in the personal care composition may vary widely. It should be appreciated that the active ingredients of the personal care compositions disclosed herein may include those ingredients capable of or configured to facilitate, promote, enhance, or otherwise increase the production or formation of natural moisturizing factors (NMFs) and/or Caspase-14 in skin, thereby increasing hydration and barrier functions of the skin. In at least one example, the active ingredients include, consist essentially of, or consist of the one or more plant oils and the source of *Aloe vera*. In a preferred implementation, the active ingredients include flaxseed oil and *Aloe vera* and/or an extract thereof. In at least one implementation, the total amount of the active ingredients present in the personal care composition may be from greater than 0 weight % to less than or equal to about 40 weight %, less than or equal to about 30 weight %, less than or equal to about 20 weight %, less than or equal to about 10 weight %, less than or equal to about 9 weight %, less than or equal to about 8 weight %, less than or equal to about 7 weight %, less than or equal to about 6 weight %, less than or equal to about 5 weight %, less than or equal to about 4 weight %, less than or equal to about 3 weight %, less than or equal to about 2 weight %, less than or equal to about 1 weight %, less than or equal to about 0.9 weight %, less than or equal to about 0.8 weight %, less than or equal to about 0.7 weight %, less than or equal to about 0.6 weight %, less than or equal to about 0.5 weight %, less than or equal to about 0.4 weight %, less than or equal to about 0.3 weight %, less than or equal to about 0.2 weight %, less than or equal to about 0.1 weight %, less than or equal to about 0.01 weight %, less than or equal to about 0.001 weight %, less than or equal to about 0.0001 weight %, less than or equal to about 9E-5 weight %, less than or equal to about 8E-5 weight %, less than or equal to about 7E-5 weight %, less than or equal to about 6.875E-5 weight %, less than or equal to about 6.5E-5 weight %, less than or equal to about 6E-5 weight %, less than or equal to about 5.5E-5 weight %, less than or equal to about 5E-5 weight %, or less than or equal to about 4.5E-5 weight %, based on a total weight of the personal care composition. In an exemplary implementation, the active ingredients include flaxseed oil and *Aloe vera* and/or an extract in a total weight % of about 0.01 weight % to about 10 weight %, based on a total weight of the personal care composition.

The personal care composition may include the one or more plant oils and the source of *Aloe vera* dispersed in, mixed with, dissolved in, combined with, or otherwise contacted with the carrier. In at least one implementation, the carrier may be capable of or configured to store, entrain, or otherwise contain the plant oils and the source of *Aloe vera*, and deliver the plant oils and the source of *Aloe vera*. It should be appreciated that the components or contents of the carrier and the respective amount of each of the components of the carrier may be at least partially determined by the type or use of the personal care product or the composition thereof. Illustrative personal care products or compositions thereof that may include the plant oils and the source of *Aloe vera* may include, but are not limited to, antiperspirants, deodorants, body washes, shower gels, soaps, including bar soaps and liquid soaps (e.g., liquid hand soaps), face washes, shampoos, hair conditioners, lotions, moisturizers, serums, spot treatments, cosmetics, or the like. In a preferred implementation, the personal care product or the composition thereof that includes the one or more plant oils and the source of *Aloe vera* are solid cleansing compositions, such as bar soaps.

In at least one implementation, the personal care product or the composition thereof may be a skin care product. Illustrative skin care product may be or include, but are not limited to, a lotion, a cosmetic, a sunscreen, or the like. The carrier of the skin care product may include, but is not limited to, any one or more of surfactants, conditioning agents, moisturizers, sunscreens, UV absorbers, antioxidants, enzymes and/or other proteins, vitamins, antibacterial agents, odor reducing agents, steroids, anti-inflammatory agents, naturally and/or non-naturally occurring humectants, skin lipid fluidizers, occlusive agents, amino acids, physical and/or chemical exfoliants, skin whiteners, anti-aging, antiperspirant actives, or the like, or any combination thereof.

In at least one implementation, the personal care product or the composition thereof may be a personal hand and/or body cleansing composition or a personal hand and/or body conditioning composition. Illustrative personal hand and/or body cleansing or conditioning compositions may include, but are not limited to, liquid soaps, bar soaps, body washes, shower gels, lotions, and the like. In a preferred implementation, the personal hand and/or body cleansing or conditioning composition is a solid personal hand and/or solid body cleansing or conditioning composition, such as bar soap. The carrier for the personal hand and/or body cleansing composition or the personal hand and/or body conditioning composition may include, but is not limited to, any one or more of fragrances, essential oils, emulsifying agents, thickening agents, colorants, surfactants, natural actives, therapeutic actives, stain prevention actives, antimicrobial agents, vitamins, natural extracts, amino acids, enzymes and/or other proteins, abrasives, odor control agents, conditioning agents, moisturizers, humectants, occlusive agents, skin lipid fluidizers, lipophilic actives, hydrophilic materials, pearlizers, opacifying agents, sodium soaps, titanium dioxide, fragrances, or the like, or any mixture or combination thereof, in addition to any one or more of the other carrier components as discussed above.

The carrier may be hydrophilic or hydrophobic. The carrier may be anhydrous. The carrier may be a liquid or a solid at room temperature. The carrier may have a viscosity of from about 2,000 centipoise (cP) to about 100,000 cP. For example, the carrier for a shower gel may have a viscosity of from about 2,000 cP to about 16,000 cP. In another example, the carrier for a lotion may have a viscosity of from about 10,000 cP to about 100,000 cP. Accordingly, it should be appreciated that the viscosity of the carrier may vary and may at least partially depend on the type of personal care composition. In an exemplary implementation, the carrier is a solid at room temperature.

Unless otherwise specifically identified, the ingredients for use in the compositions and formulations of the compositions disclosed herein are preferably cosmetically acceptable ingredients. As used herein, the expression "cosmetically acceptable" may refer to a component or ingredient that is suitable for use in a formulation for topical application to human skin. A cosmetically acceptable excipient, may refer to an excipient that is suitable for external application in the amounts and concentrations contemplated in the formulations of the compositions disclosed herein, and includes for example, excipients which are "Generally Recognized as Safe" (GRAS) by the United States Food and Drug Administration (FDA).

METHODS

The present disclosure may provide methods for preparing a personal care product or a personal care composition thereof. In at least one implementation, the method may include mixing, stirring, combining, or otherwise contacting a carrier, one or more plant oils, and the source of *Aloe vera* with one another. In another implementation, the method may include adding, mixing, stirring, combining, or otherwise contacting one or more plant oils and the source of *Aloe vera* with a carrier. In at least one example, the carrier is a base solid cleansing composition. For example, the carrier may be a bar soap. In another implementation, the carrier is a base liquid cleansing composition. For example, the carrier may be a liquid soap, a shower gel, or the like.

The present disclosure may further provide methods for treating one or more skin conditions, such as one or more dry skin conditions. Illustrative dry skin conditions may be or include, but are not limited to, atopic dermatitis, rosacea, psoriasis, or the like. It should be appreciated that atopic dermatitis may result in a deficiency of filaggrin (filament-aggregating protein), a protein at least partially responsible for skin barrier functions and NMF production. It should further be appreciated that filaggrin contributes to the physical strength of the stratum corneum (SC) barrier through its integral involvement in the filament matrix complex in the inner layer of the stratum corneum (SC). In the outer layer of the SC, filaggrin is degraded into NMFs. It should be appreciated that NMFs are integral to the function of the SC as NMFs provide moisture retention (humectancy), maintain the acidic pH and buffering capacity of the SC, promote proper epidermal maturation and desquamation, and decrease pathogenic bacterial colonization.

The method for treating the one or more skin conditions may include increasing amounts of natural moisturizing factors (NMFs) in skin by contacting any one or more of the personal care compositions disclosed herein with the skin. The method may include increasing production or amount of a Caspase-14 gene in the skin to promote filaggrin degradation to thereby produce NMF in the skin.

The method for treating one or more skin conditions may also include diagnosing or determining the presence of the one or more skin conditions. Diagnosing or determining the presence of the one or more skin conditions may include measuring a deficiency of natural moisturizing factors (NMFs) in skin, a deficiency of filaggrin in skin, and/or reduced levels of Caspase-14 in skin. The deficiency of NMFs in skin may be measured and compared with relative amounts of NMFs in a population baseline value or a previous individual baseline value. The deficiency of filaggrin in skin may be measured and compared with relative amounts of filaggrin in a population baseline value or a previous individual baseline value. Similarly, the reduced levels of Caspase-14 in skin may be measured and compared with relative amounts of filaggrin in a population baseline value or a previous individual baseline value. It should be appreciated that the population baseline value may be the value from a population that does not have any one or more of the aforementioned skin conditions. The decreased or reduced levels of NMFs, filaggrin, and/or Caspase-14 may be at least 1% less than, at least 2% less than, at least 5% less than, at least 8% less than, at least 10% less than, at least 12% less than, at least 15% less than, at least 20% less than, at least 25% less than, at least 30% less than, at least 40% less than, at least 50% less than, at least 60% less than, at least 70% less than, at least 80% less than, at least 90% less than, at least 100% less than, at least 150% less than, at least 200% less than, at least 250% less than, at least 300% less than, at least 400% less than, or at least 500% less than the population baseline value or the previous individual baseline value.

The present disclosure may also provide a personal care composition including a carrier, one or more plant oils, and the source of *Aloe vera* (i.e., *Aloe vera* and/or an extract thereof) for use in treating one or more dry skin conditions. The personal care composition may be contacted with the skin to treat the one or more dry skin conditions.

The present disclosure may also provide methods of cleansing skin and/or enhancing hydration and barrier functions of the skin in a patient in need thereof by enhancing the production of Caspase-14 and/or NMF. Patients in need thereof may have relatively lower natural moisturizing factors (NMFs) and/or relatively low amounts or concentration of Caspase-14 in the skin, which may be evidenced by dry and/or chapped skin. The method may include providing an effective amount of the personal cleansing composition to enhance Caspase-14 and/or NMF in skin, contacting the personal cleansing composition to the skin or hair, and optionally, rinsing the personal cleansing composition from the skin or hair with water. In at least one embodiment, the personal cleansing composition may be combined with added water prior to or while contacting the personal cleansing composition with the skin or hair.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

A base solid cleansing composition having a pH of from about 9 to about 10 was prepared. A control solid cleansing composition (1) and three test solid cleansing compositions (2)-(4) were then prepared by adding varying amounts of flaxseed oil and/or *Aloe vera* to the base solid cleansing composition according to Table 1. Each of the solid cleansing compositions (1)-(4) was tested as an about 1% soap samples. Particularly, each of the solid cleansing compositions (1)-(4) was diluted in water in a weight ratio of about 1:20, and subsequently diluted in phosphate-buffered saline (PBS) in a weight ratio of about 1:5.

TABLE 1

Compositions of Control and Test Solid Cleansing Compositions (1)-(4)

| # | Amount of Base Solid Cleansing Composition (wt %) | Amount of Flaxseed Oil (FSO) (wt %) | Amount of Aloe Vera (AV) (wt %) |
|---|---|---|---|
| 1 | 100 | 0 | 0 |
| 2 | 99.5 | 0.5 | 0 |
| 3 | 99.5 | 0 | 0.5 |
| 4 | 99.0 | 0.5 | 0.5 |

Example 2

Each of the control and test solid cleansing compositions (1)-(4) was evaluated in vitro on skin tissue models to observe the production of natural moisturizing factors (NMFs), particularly via measuring biomarker Caspase-14. It should be appreciated that an increase or decrease in the amount of biomarker Caspase-14 indicates increased or decreased production of NMF, respectively, as Caspase-14 is utilized in the degradation of filaggrin to produce NMF in skin. 3D human skin models obtained from MatTek Corp. of Ashland, MA, were utilized as the models in the in vitro study, and the Caspase-14 production was monitored with an ELISA Kit.

To conduct the in vitro study, 30 μm of each of the dilute solutions of the control solid cleansing composition (1) or the test solid cleansing compositions (2)-(4) was topically applied to respective 3D human skin models and incubated at about 37° C. for about 1 hour. After about 1 hour, each of the 3D human skin models was thoroughly and gently washed with PBS about 5 to about 8 times. Each of the 3D human skin models was then placed in fresh media and incubated at about 37° C. for about 24 hours. The 3D human skin models were then collected and lysed with (Heat Shock Protein) lysis buffer, and the 3D human skin models were broken down with a shaker at a speed of about 15.01/s for 15 minutes twice. After lysing with the HSP lysis buffer, each of the lysed samples were frozen or maintained at about −80° C. The production of NMF biomarker Caspase-14, as measured by the ELISA kit, from respective human skin models treated with each of the control and test liquid cleansing compositions (1)-(4) is summarized in Table 2. All measurements were done in triplicate, averaged, and normalized to the total protein in each of the 3D human skin models.

TABLE 2

Amount of Caspase-14 Measured from Skin Models Treated with Control and Test Solid Cleansing Compositions (1)-(4)

| # | Amount of Flaxseed Oil (wt %) | Amount of Aloe Vera (wt %) | Amount of Caspase-14 | Std Dev | Change from Control |
|---|---|---|---|---|---|
| 1 | 0 | 0 | 374.4 | 22.6 | — |
| 2 | 0.5 | 0 | 302.8 | 31.9 | −71.6 |
| 3 | 0 | 0.5 | 339.8 | 35.3 | −34.6 |
| 4 | 0.5 | 0.5 | 428.4 | 21.0 | 54.0 |

As illustrated in Table 2, the test solid cleansing composition (2) including only flaxseed oil exhibited a decrease in the amount of Caspase-14 relative to the control cleansing composition (1). As further illustrated in Table 2, the test solid cleansing composition (3) including only *Aloe vera* also exhibited a decrease in the amount of Caspase-14 relative to the control cleansing composition (1). However, surprising and unexpected, the synergistic combination of flaxseed oil and *Aloe vera* in test solid cleansing composition (4) exhibited a significant increase in Caspase-14. The observed increase in Caspase-14 in test cleansing composition (4) is especially surprising and unexpected as each of flaxseed oil and *Aloe vera*, when evaluated separately, exhibited a decrease in Caspase-14. Accordingly, a decrease in Caspase-14 was expected, not the observed increase in Caspase-14. As noted above, it should be appreciated that an increase in the amount of biomarker Caspase-14 indicates the production of NMF, as Caspace-14 is utilized in the degradation of filaggrin to produce NMF in skin.

Example 3

A base solid cleansing composition having a pH of from about 9 to about 10 was prepared. A control solid cleansing composition (5) and five test solid cleansing compositions (6)-(10) were then prepared by adding varying amounts of flaxseed oil and/or *Aloe vera* to the base solid cleansing composition according to Table 3. Each of the solid cleansing compositions (5)-(10) was tested as an about 1% soap samples. Particularly, each of the solid cleansing compositions (5)-(10) was diluted in water in a weight ratio of about 1:20, and subsequently diluted in phosphate-buffered saline (PBS) in a weight ratio of about 1:5.

Each of the control and test solid cleansing compositions (5)-(10) was evaluated in vitro on skin tissue models to observe the production of natural moisturizing factors (NMFs), particularly via measuring biomarker Caspase-14, as discussed above with respect to Example 2. It should be appreciated that a separate control was utilized since a separate 3D human skin model was tested. It should further be appreciated that the normalized data of one 3D human skin sample may be compared to the data of another 3D human skin sample. The production of NMF biomarker Caspase-14, as measured by the ELISA kit, from respective human skin models treated with each of the control and test liquid cleansing compositions (5)-(20) is summarized in Table 3. All measurements were done in triplicate, averaged, and normalized to the total protein in each of the 3D human skin models.

TABLE 3

Amount of Caspase-14 Measured from Skin Models Treated with Control and Test Solid Cleansing Compositions (5)-(10)

| # | Amount of Flaxseed Oil (wt %) | Amount of Aloe Vera (wt %) | Amount of Caspase-14 | Std Dev | Change from Control |
|---|---|---|---|---|---|
| 5 | 0 | 0 | 367.9 | 112.3 | — |
| 6 | 0.5 | 0 | 307.3 | 47.9 | −16.5 |
| 7 | 0 | 0.25 | 388 | 74.7 | 5.5 |
| 8 | 0.5 | 0.25 | 393.1 | 135.4 | 6.8 |
| 9 | 0 | 0.75 | 351.6 | 48.1 | −4.4 |
| 10 | 0.5 | 0.75 | 412 | 30.6 | 12 |

As illustrated in Table 3, the test solid cleansing composition (6) including only flaxseed oil exhibited a decrease in the amount of Caspase-14 relative to the control cleansing composition (5). As further illustrated in Table 3, the test solid cleansing composition (7) including only *Aloe Vera* in an amount of about 0.25 wt % exhibited an increase in the amount of Caspase-14 relative to the control cleansing composition (5). Further, the test solid cleansing composition (9) including *Aloe Vera* in an amount of about 0.75 wt % exhibited a decrease in the amount of Caspase-14 relative to the control cleansing composition (5). The test solid cleansing compositions (7) and (9) suggest that *Aloe Vera* alone only exhibits increased Caspase-14 when present in an amount of less than 0.75 wt %. As such, it was surprisingly and unexpectedly discovered that when FSO in an amount of at least 0.5 wt % was combined with 0.75 wt % *Aloe Vera*, as in test solid cleansing composition (10), an increase in the amount of Caspase-14 was observed. The observed increase in Caspase-14 in test cleansing composition (10) is especially surprising and unexpected as both *Aloe Vera* in an amount of 0.75 wt % (9) and Flaxseed oil in an amount of 0.5 wt %, when evaluated separately, exhibited a decrease in Caspase-14. Accordingly, a decrease in Caspase-14 was expected, not the observed significant increase in Caspase-14. As noted above, it should be appreciated that an increase in the amount of biomarker Caspase-14 indicates the production of NMF, as Caspace-14 is utilized in the degradation of filaggrin to produce NMF in skin.

Example 4

Another base solid cleansing composition having a pH of from about 9 to about 10 was prepared. A control solid cleansing composition (11) and two test solid cleansing compositions (12) and (13) were then prepared by adding varying amounts of flaxseed oil and/or *Aloe vera* to the base solid cleansing composition according to Table 4. Each of the solid cleansing compositions (11)-(13) was tested as an about 1% soap samples. Particularly, each of the solid cleansing compositions (11)-(13) was diluted in water in a weight ratio of about 1:20, and subsequently diluted in phosphate-buffered saline (PBS) in a weight ratio of about 1:5.

Each of the control and test solid cleansing compositions (11)-(13) was evaluated in vitro on skin tissue models to observe the production of natural moisturizing factors (NMFs), particularly via measuring biomarker Caspase-14, as discussed above with respect to Example 2. As discussed above, it should be appreciated that a separate control was utilized since a separate 3D human skin model was tested, and the normalized data of one 3D human skin sample may be compared to the data of another 3D human skin sample. The production of NMF biomarker Caspase-14, as measured by the ELISA kit, from respective human skin models treated with each of the control and test liquid cleansing compositions (11)-(13) is summarized in Table 4. All measurements were done in triplicate, averaged, and normalized to the total protein in each of the 3D human skin models.

TABLE 4

Amount of Caspase-14 Measured from Skin Models Treated with Control and Test Solid Cleansing Compositions (11)-(13)

| # | Amount of Flaxseed Oil (wt %) | Amount of Aloe Vera (wt %) | Amount of Caspase-14 | Std Dev | Change from Control |
|---|---|---|---|---|---|
| 11 | 0 | 0 | 373.4 | 183.6 | — |
| 12 | 0.5 | 0.125 | 341.2 | 102.7 | −32.2 |
| 13 | 0.5 | 1 | 366.3 | 68.3 | −7.1 |

As illustrated in Table 4, when FSO is present in an amount of 0.5 wt % and *Aloe Vera* is present in an amount of about 0.125 wt % (as in test composition 12) or in an amount of about 1 wt % (as in test composition 13), a synergistic increase in the amount of Caspase-14 was not observed. Without being bound by theory, it is believed that when FSO is present in an amount of about 0.5 wt %, *Aloe Vera* should be present in an amount of about 0.125 wt % or greater and about 1 wt % or less to exhibit the surprising and unexpected result of increased Caspace-14. Additionally, without being bound by theory, it is believed that a flaxseed oil to *Aloe Vera* ratio (FSO:AV) of greater than about 1:0.25 and less than about 1:2 would exhibit the surprising and unexpected result of increased Caspace-14. Each of the test solid cleansing compositions disclosed herein (4), (8), (9), (12), and (13) that included the combination of FSO and *Aloe Vera* support the ratio of FSO:AV of about 1:0.25 (4:1) or greater and about 1:2 (0.5:1) or less for increasing Caspace-14.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A personal care composition, comprising:
   a carrier;
   one or more plant oils comprising flaxseed oil; and
   an *aloe vera* extract present in an amount of from about 0.125 weight % to about 1 weight %;
   wherein the one or more plant oils are present in an amount of about 0.5 weight %, based on a total weight of the personal care composition.

2. The personal care composition of claim 1, wherein the *aloe vera* extract and the one or more plant oils are each present in an effective amount to increase natural moisturizing factors in skin when applied to the skin.

3. The personal care composition of claim 1, wherein the *aloe vera* extract is selected from the group consisting of a liquid extract, a gel obtained directly from the leaves of an *Aloe vera* plant, and a gel reconstituted from powdered *aloe vera* extract.

4. The personal care composition of claim 3, wherein the *aloe vera* extract comprises a liquid *aloe vera* extract.

5. The personal care composition of claim 1, wherein the one or more plant oils and the *aloe vera* extract are present in an effective ratio to increase natural moisturizing factors in skin when applied to the skin, wherein the one or more plant oils and the *aloe vera* extract are present in a ratio of from about 0.1:1 to about 2:1, from about 0.5:1 to about 1.5:1, or about 1:1.

6. The personal care composition of claim 1, wherein the personal care composition is a personal cleansing composition, wherein the personal cleansing composition is a shower gel or a bar soap.

7. The personal care composition of claim 1, wherein the carrier is a solid carrier.

8. The personal care composition of claim 1, wherein the carrier is a liquid carrier.

9. The personal care composition of claim 3, wherein the *aloe vera* extract comprises a gel obtained directly from the leaves of an *Aloe vera* plant.

10. The personal care composition of claim 3, wherein the *aloe vera* extract comprises a gel reconstituted from powdered *aloe vera* extract.

11. A method for preparing the personal care composition of claim 1, the method comprising contacting the one or more plant oils, the *Aloe vera* extract, and the carrier with one another.

12. A method for treating one or more dry skin conditions, the method comprising contacting skin with the personal care composition of claim 1.

13. The method of claim 12, wherein contacting the skin with the personal care composition of claim 1 increases an amount of natural moisturizing factors in or on the skin.

14. The method of claim 12, wherein contacting the skin with the personal care composition of claim 1 increases an amount of Caspase-14 in or on the skin.

15. The method of claim 12, further comprising determining the presence of the one or more dry skin conditions.

16. The method of claim 15, wherein determining the presence of the one or more dry skin conditions comprises measuring a deficiency of filaggrin, natural moisturizing factors, and/or Caspase-14 levels in skin.

17. The method of claim 16, wherein the deficiency of filaggrin, natural moisturizing factors, and/or Caspase-14 levels in skin is measured relative to a population baseline value.

18. The method of claim 16, wherein the deficiency of filaggrin, natural moisturizing factors, and/or Caspase-14 levels in skin is measured relative to an individual baseline value.

* * * * *